US00PP08156P

United States Patent [19]

Austin

[11] Patent Number: Plant 8,156

[45] Date of Patent: Feb. 23, 1993

[54] ROSE PLANT—'AUSRAM'

[75] Inventor: David C. H. Austin, Albrighton, England

[73] Assignee: David Austin Roses, Wolverhampton, England

[21] Appl. No.: 623,306

[22] Filed: Dec. 6, 1990

[51] Int. Cl.[5] ..... A01H 5/00

[52] U.S. Cl. ..... Plt./1

[58] Field of Search ..... Plt./1, 23

*Primary Examiner*—Howard J. Locker

*Attorney, Agent, or Firm*—Ladas & Parry

[57] ABSTRACT

A new variety of rose plant of the shrub class distinctive in its character by its fully double, soft faintish yellowish white and pale yellow/faint pink flowers giving an overall white effect with abundant continual blooming, and the unusual shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention): Ausram.

*Cultivar trade name.*—Francine Austin.

*Type.*—Hardy, bushy, outdoor, garden decoration, cut flowers.

*Class.*—Shrub.

Propagation: This variety holds its distinguishing characteristics through succeeding propagations by budding.

Asexual reproduction of the new cultivar by budding has taken place at a nursery in Albrighton, Nr. Wolverhampton, England and was derived as follows:

Female parent (seed parent): Alister Stella Gray (non-patented).

Male parent (pollen parent): Ballerina (non-patented).

The operation of the artificial pollination is therefore expressed by the following Alister Stella Gray×Ballerina.

The following observations are made of specimens grown outdoors in England.

PLANT DESCRIPTION

Plant:

*Height.*—90 cm.

*Habit.*—Bushy and sprawling.

Branches:

*Young stems.*—Color: 30E8 parrot green faint red blushing and spotting on one side of stem. Texture: Smooth. Thorns: Lower nodes with occasional red thorns, downwards pointing wide base.

*Old stems.*—Color: 29D7-8 deep/greyish green. Texture: Smooth. Thorns: Glabrous, occasional brownish red thorns on lower nodes.

LEAVES

Stipules:

*Length.*—15–20 mm.

*Width.*—4–7 mm.

*Angle of wingtips to petiole.*—About 45° to petiole and downwardly curved.

*Color.*—Greyish green 30A4.

*Margins.*—Pectinate and teeth have red tips.

*Shape.*—Long and narrow.

Petiole:

*General description.*—Length: 2.1 cm. Upperside color: Slender and deep green 29E6, reddish groove. Groove/hairs/thorns: Small thorns. Underside: Paler green, glabrous and sparse downwardly pointed. Hair/thorns: Very occasional reddish glandular hairs.

Leaflets:

*Number.*—3–7 (mainly 7).

*Shape.*—Lanceolate.

*Serration.*—Serrate with cuspidate apex.

*Texture.*—Leathery.

General effect of foliage: Medium dense and semi glossy.

Color:

*Young foliage.*—Upperside: Olive 1E6, tips of serrations deep red. Underside: Olive 1E5 with blotchy reddish blush, a slightly potted effect.

*Adult foliage.*—Upperside: 29F7 dark green. Underside: 29E6 spinach green.

INFLORESCENCE

Number of flowers per stem: Numerous: Variable, but in the range of 40 to 80.

Peduncle:

*Length.*—Variable 3.0–4.5 cm.

*Color.*—Base pale/pastel green 29A 3–4 blushed with pale/pastel red 10A 3–4 deepening to geranium red 11B7 at edges.

*Thorns/hairs.*—There are thorns/hairs on some outer petals.

Sepals:

*Upperside color.*—Tomentose, deep green 30E8 with variable reddish blotching and blushing.

*Outer margins.*—Ensiform protrusions and sparse red glandular hair.

*Inner margins.*—Entire densely tomentose.

*Underside color.*—As upper side but more densely tomentose.

*Outside texture.*—Finely hairy.

*Sepal length.*—1.0 cm.

Bud:

*Shape.*—Oval with rounded base and cuspidate apex.

*Length.*—0.75 to 1.25 cm.

*Max. width.*—0.4 cm.

*Color when opening.*—Base pale/pastel green 29A3/4 blushed with pale/pastel red 10A3/4 deepening to geranium red 11B7 at edges of some outer petals.

Flower:

*Shape.*—Very flattened top, outer petals curling down towards stem.

*Diameter.*—3 to 4 cm.

*Color when opening.*—Upperside: Outer petals: 1A3 pale yellow faintly blushed with pink towards center of top. Basal tip yellow 2A4. Inner petals: White to faint yellowish white. Fair pink blush paler than 9A2 towards top. Yellow basal 2A4. Underside: Outer petals: 1A3 pale yellow blushed with pinkish white around centre top. Inner petals: Same as upper side but pink blush more pronounced.

*Color when blooming.*—Upperside: Yellowish white 1A3 but pink tinge less pronounced. More obvious in center petals. Basal tips of orange yellow shadings. Underside: Pale yellow 2A2 to faint pinkish 14A2.

*Coloring when finished blooming.*—Upperside: Outer petals: Faint yellowish white 1A2. Basal tip pale yellow 2A2. Inner petals: As outer petals. Underside: Outer petals: Faint yellowish white 1A2. Inner petals: Very faint pink 11A2 and blush on center of petal.

Length of season of blooming at production location: From June to November.

Fragrance: Good and musk type.

Lasting quality: Good, lasting for 10–14 days on the plant and 7–10 days as cut flowers.

Petals:

*Shape.*—Outside: Very outside petals are rounded with obtuse base and smooth round tops. Inside: Ovoid with flattish top and acute base.

*Texture.*—Soft and silky.

*Number.*—45–55, inner 5–10 exhibit staminody.

*Cleaning.*—Good, petals fall quickly to produce a tidy rose.

Stamens:

*Number.*—10–20.

*Anthers.*—Normal, bright yellow 2A6.

*Filaments.*—Yellowish 2A3 of irregular heights.

Pistils:

*Number.*—18 average.

*Stigmas.*—Normal, straw.

*Styles.*—Greenish 1B4 some with brownish red streaks of irregular heights.

Receptacle:

*Color.*—Greyish green 28B2 with brownish red blush.

*Texture.*—Tomentose.

*Size.*—6×4 mm.

*Shape.*—Jug shaped.

THE DEVELOPMENT

Vegetation: Vigorous.

Blooming: Abundant and continual.

Aptitude to bearing fruits: None.

Resistance to frost: Good.

Resistance to disease: Very good.

I claim:

1. A new and distinct variety of rose plant of the shrub class, characterized as to novelty by its fully double flowers of faintish yellowish white and pale yellow/faint pink giving an overall white coloring with abundant and continual blooming and the unusual shaping of the flower being substantially as shown and described.

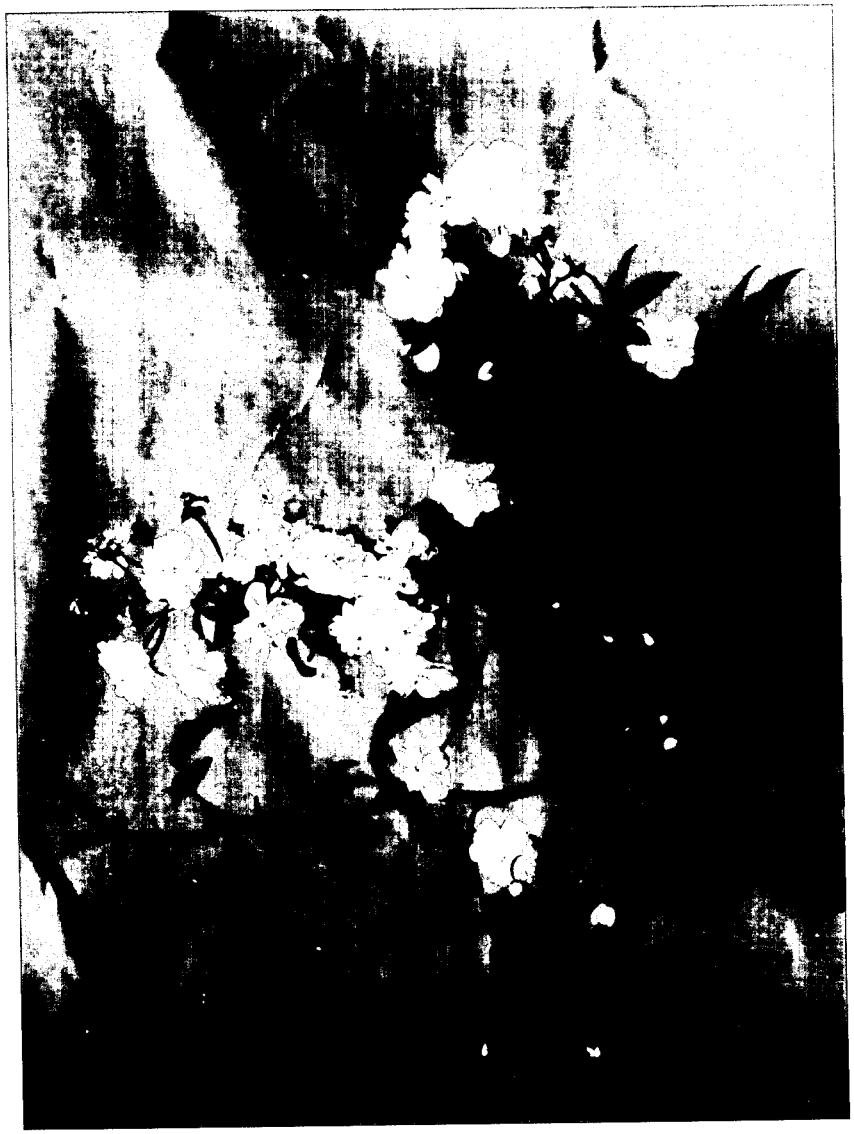

* * * * *